United States Patent
Blazejewski et al.

(10) Patent No.: US 11,052,046 B2
(45) Date of Patent: Jul. 6, 2021

(54) METHOD FOR PREPARING MICRO-PARTICLES BY DOUBLE EMULSION TECHNIQUE

(71) Applicant: NANOMI B.V., Oldenzaal (NL)

(72) Inventors: Emilie Janine Marie Blazejewski, Oldenzaal (NL); Robertus Franciscus Duwel, Oldenzaal (NL)

(73) Assignee: NANOMI B.V., Oldenzaal (NL)

( * ) Notice: Subject to any disclaimer, the term of this patent is extended or adjusted under 35 U.S.C. 154(b) by 0 days.

(21) Appl. No.: 16/651,050

(22) PCT Filed: Sep. 26, 2018

(86) PCT No.: PCT/NL2018/050636
§ 371 (c)(1),
(2) Date: Mar. 26, 2020

(87) PCT Pub. No.: WO2019/066649
PCT Pub. Date: Apr. 4, 2019

(65) Prior Publication Data
US 2020/0230061 A1    Jul. 23, 2020

(30) Foreign Application Priority Data
Sep. 26, 2017  (NL) .................................. 2019632

(51) Int. Cl.
*A61K 9/16* (2006.01)
*A61K 9/50* (2006.01)
(Continued)

(52) U.S. Cl.
CPC .......... *A61K 9/1694* (2013.01); *A61K 9/5031* (2013.01); *A61K 9/0024* (2013.01);
(Continued)

(58) Field of Classification Search
CPC .... A61K 9/1694; A61K 9/5031; A61K 38/23; A61K 9/0024; A61K 38/31; A61K 38/09
See application file for complete search history.

(56) References Cited

U.S. PATENT DOCUMENTS

| | | |
|---|---|---|
| 4,389,330 A | 7/1983 | Tice et al. |
| 4,652,441 A | 3/1987 | Okada et al. |

(Continued)

FOREIGN PATENT DOCUMENTS

| | | |
|---|---|---|
| EP | 0052510 | 5/1982 |
| WO | 2010085607 | 7/2010 |

(Continued)

*Primary Examiner* — Robert A Wax
*Assistant Examiner* — Quanglong N Truong
(74) *Attorney, Agent, or Firm* — Duane Morris LLP; Gregory M. Lefkowitz; Brandon A. Chan

(57) ABSTRACT

Methods for preparing micro-particles using a double emulsion technique combining a membrane and a micro-sieve are provided. Particularly the present invention relates to method for preparing micro-particles comprising: preparing a first phase comprising an active agent; preparing a second phase comprising a carrier and a solvent; passing the first phase and the second phase through a membrane to form a primary emulsion; passing the primary emulsion through a micro-sieve in a continuous phase to form a secondary emulsion; and removing the solvent to form the micro-particles.

14 Claims, 4 Drawing Sheets

(51) Int. Cl.
*A61K 9/00* (2006.01)
*A61K 38/09* (2006.01)
*A61K 38/23* (2006.01)
*A61K 38/31* (2006.01)

(52) U.S. Cl.
CPC .............. *A61K 38/09* (2013.01); *A61K 38/23* (2013.01); *A61K 38/31* (2013.01)

(56) References Cited

U.S. PATENT DOCUMENTS

| | | | |
|---|---|---|---|
| 4,673,595 | A | 6/1987 | Orsolini et al. |
| 5,134,122 | A | 7/1992 | Orsolini |
| 5,192,741 | A | 3/1993 | Orsolini et al. |
| 5,225,205 | A | 7/1993 | Orsolini |
| 5,431,348 | A | 7/1995 | Orsolini et al. |
| 5,439,688 | A | 8/1995 | Orsolini et al. |
| 5,445,832 | A | 8/1995 | Orsolini et al. |
| 5,776,885 | A | 7/1998 | Orsolini et al. |
| 5,945,126 | A | 8/1999 | Thanoo et al. |
| 2006/0220269 | A1* | 10/2006 | Noritomi ................. B01J 13/04 264/4.1 |
| 2009/0104274 | A1* | 4/2009 | Khopade .............. A61K 9/1647 424/490 |
| 2010/0069602 | A1* | 3/2010 | Raiche ................. A61K 31/573 528/354 |

FOREIGN PATENT DOCUMENTS

| | | |
|---|---|---|
| WO | 2011087689 | 7/2011 |
| WO | 2011089595 | 7/2011 |
| WO | 2011119903 | 9/2011 |

* cited by examiner

Interwoven fiber (IWF)

Open cell structure (OCS)

Micro-sieve

METHOD FOR PREPARING MICRO-PARTICLES BY DOUBLE EMULSION TECHNIQUE

FIELD OF THE INVENTION

The present invention relates to a method for preparing micro-particles having a uniform size and narrow size distributions. The present invention further relates to a method for preparing micro-particles using a double emulsion technique combining a membrane and a micro-sieve.

BACKGROUND OF THE INVENTION

Encapsulation of pharmaceutically active agents into micro-particles of polymers can prolong the therapeutic drug levels in the blood. The release of active agents may be extended up to several months depending on the type of polymer and the active agents encapsulated.

A number of approaches have been used to encapsulate active agents into micro-particles of polymers for sustained release. Most of them are based on phase separation (U.S. Pat. No. 4,673,595, European Patent No. 0,052,510), cryopulverization after melt extrusion (U.S. Pat. Nos. 5,134,122, 5,192,741, 5,225,205, 5,431,348, 5,439,688, 5,445,832 and 5,776,885) and single emulsion evaporation (oil/water) (U.S. Pat. Nos. 4,389,330 and 5,945,126).

Poorly water soluble or hydrophobic drugs are successfully retained within the micro-particles prepared by above said approaches. However, the encapsulation of water soluble or hydrophilic drugs presents difficult challenge due to low encapsulation efficiency. The problem of inefficient encapsulation of hydrophilic drugs can be overcome by using double emulsification technique.

The double emulsion technique for preparation of micro-particles involves the formation of multiple emulsions like w/o/w, o/w/o, s/o/w, w/o/o and s/o/o etc. (w: water, o: oil, s: solid). This method can be used for the encapsulation of both hydrophilic and hydrophobic drugs. In particular, water-oil-water (w/o/w) type of double emulsion technique has commonly been applied to encapsulate hydrophilic drugs such as peptides, proteins, vaccines and nucleic acids into polymeric microspheres in micro- or nano-scale form. The w/o/w method begins with the use of volatile organic solvent to dissolve the polymer and to form an oil phase. The drug aqueous solution (i.e. an aqueous phase) is dispersed in the oil phase to form a primary emulsion (w/o). The resulting primary emulsion is then added to a larger aqueous phase to prepare a secondary emulsion (w/o/w). The secondary emulsion is then stirred for several hours which allows the organic solvent to evaporate and the micro-particles to harden.

U.S. Pat. No. 4,652,441 discloses a w/o/w method for producing a prolonged release microcapsule, which comprises preparing a water-in-oil (w/o) emulsion comprising an inner aqueous layer containing a biologically active polypeptide, a drug retaining substance therefor selected from a member of the group consisting of gelatin, albumin, pectin and agar and an oil layer containing a polymer substance of lactic acid-glycolic acid copolymer or lactic acid polymer, then thickening or solidifying said inner aqueous layer to a viscosity of not lower than about 5000 centipoises and finally admixing the resulting emulsion with a third aqueous layer to give a water/oil/water ternary layer (w/o/w) emulsion and then desorbing the solvent in the oil layer. The emulsification of the inner aqueous layer, oil layer and third aqueous layer can be effected by the conventional dispersion techniques. For example, intermittent shaking, mixing by means of a propeller mixer, turbine mixer or the like, colloid mill operation, mechanical homogenization, ultrasonication, etc. may be utilized.

Such conventional dispersion techniques have several limitations. For example, these techniques utilize the turbulent flow conditions for the preparation of emulsion by creating varying areas of turbulence in the vessel. As a result, some areas of the vessel produce a higher turbulence (typically closer to the blades and walls), while other areas produce lower turbulence (further away from blades and walls). Varying turbulence within the vessel results in difficulty in controlling the size of the resulting primary emulsion and secondary emulsion and that eventually leads to wide size distributions and batch to batch variations of obtained micro-particles sizes. Since the size distributions and size of the micro-particles directly affect the drug release rate and syringeability, it is important that the particle size distributions and size be relatively narrow and uniform.

Use of conventional dispersion techniques also presents problems when preparing micro-particles containing certain active agents, such as proteins, peptides and biological agents which are very sensitive to turbulence and high shear forces. Long time exposures to high shear can lead to deactivation (e.g. protein unfolding or aggregation) and degradation of the active agent.

In order to overcome such limitations, the present invention describes a method for preparing micro-particles by utilizing laminar flow conditions which minimizes the mechanical agitation and turbulence during mixing of aqueous phase and oil phase. The reproducibility, the control over emulsion globule size and the stability of the primary emulsion are improved which consistently provides a uniform size and narrow size distributions of micro-particles.

SUMMARY OF THE INVENTION

An aspect of the present invention provides a method for preparing a stable primary emulsion comprising: (a) preparing a first phase comprising an active agent; (b) preparing a second phase comprising a carrier; and (c) passing the first phase and the second phase through a membrane to form the stable primary emulsion.

An aspect of the present invention provides a method for preparing a stable primary emulsion comprising: (a) preparing a first phase comprising an active agent; (b) preparing a second phase comprising a carrier; and (c) passing the first phase and the second phase through an interwoven fiber to form the stable primary emulsion.

Another aspect of the present invention provides a method for preparing a secondary emulsion comprising: (a) preparing a first phase comprising an active agent; (b) preparing a second phase comprising a carrier; (c) passing the first phase and the second phase through a membrane to form a primary emulsion; and (d) passing the primary emulsion through a micro-sieve in a continuous phase to form the secondary emulsion.

Another aspect of the present invention provides a method for preparing micro-particles comprising: (a) preparing a first phase comprising an active agent; (b) preparing a second phase comprising a carrier and a solvent; (c) passing the first phase and the second phase through a membrane to form a primary emulsion; (d) passing the primary emulsion through a micro-sieve in a continuous phase to form a secondary emulsion; and (e) removing the solvent to form the micro-particles.

Another aspect of the present invention provides a method for preparing micro-particles comprising: (a) preparing a first phase comprising an active agent; (b) preparing a second phase comprising a carrier and a solvent; (c) passing the first phase and the second phase through an interwoven fiber to form a primary emulsion; (d) passing the primary emulsion through a micro-sieve in a continuous phase to form a secondary emulsion; and (e) removing the solvent to form the micro-particles.

An aspect of the present invention provides a method for preparing micro-particles comprising:
(a) preparing a first phase comprising leuprolide acetate as an active agent; (b) preparing a second phase comprising a carrier and a solvent; (c) passing the first phase and the second phase through an interwoven fiber to form a primary emulsion; (d) passing the primary emulsion through a micro-sieve in a continuous phase to form a secondary emulsion; and (e) removing the solvent to form the micro-particles.

An aspect of the present invention provides a method for preparing micro-particles comprising:
(a) preparing a first phase comprising leuprolide acetate as an active agent; (b) preparing a second phase comprising poly(d,l-lactic acid) polymer and a solvent; (c) passing the first phase and the second phase through an interwoven fiber to form a primary emulsion; (d) passing the primary emulsion through a micro-sieve in a continuous phase to form a secondary emulsion; and (e) removing the solvent to form the micro-particles.

An aspect of the present invention provides a method for preparing micro-particles comprising:
(a) preparing a first phase comprising leuprolide acetate as an active agent and water; (b) preparing a second phase comprising poly(d,l-lactic acid) polymer and dichloromethane; (c) passing the first phase and the second phase through an interwoven fiber to form a primary emulsion; (d) passing the primary emulsion through a micro-sieve in a continuous phase to form a secondary emulsion; and (e) removing the dichloromethane to form the micro-particles An aspect of the present invention provides a method for preparing micro-particles comprising:
(a) preparing a first phase comprising leuprolide acetate as an active agent; (b) preparing a second phase comprising poly lactic-co-glycolic acid polymer and a solvent; (c) passing the first phase and the second phase through an interwoven fiber to form a primary emulsion; (d) passing the primary emulsion through a micro-sieve in a continuous phase to form a secondary emulsion; and (e) removing the solvent to form the micro-particles.

An aspect of the present invention provides a method for preparing micro-particles comprising:
(a) preparing a first phase comprising an active agent; (b) preparing a second phase comprising a carrier and a solvent; (c) passing the first phase and the second phase through an open cell structure to form a primary emulsion; (d) passing the primary emulsion through a micro-sieve in a continuous phase to form a secondary emulsion; and (e) removing the solvent to form the micro-particles.

An aspect of the present invention provides a method for preparing micro-particles comprising:
(a) preparing a first phase comprising an active agent; (b) preparing a second phase comprising a carrier and a solvent; (c) passing the first phase and the second phase through a micro-sieve to form a primary emulsion; (d) passing the primary emulsion through a micro-sieve in a continuous phase to form a secondary emulsion; and (e) removing the solvent to form the micro-particles.

An aspect of the present invention provides a method for preparing micro-particles comprising:
(a) preparing a first phase comprising an active agent and a solvent; (b) preparing a second phase comprising a carrier; (c) passing the first phase and the second phase through a membrane to form a primary emulsion; (d) passing the primary emulsion through a micro-sieve in a continuous phase to form a secondary emulsion; and (e) removing the solvent to form the micro-particles.

An aspect of the present invention provides a microencapsulated active agent and micro-particles prepared by the methods of the present invention.

DETAILED DESCRIPTION OF THE INVENTION

Figure 1A:
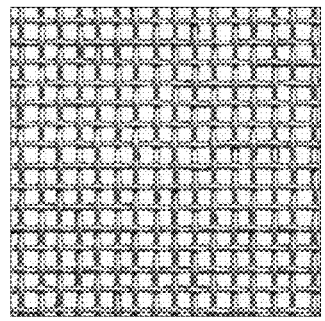
FIGS. 1A-1C show one embodiment of an interwoven fiber (IWF), an open cell structure (OCS), and a micro-sieve suitable for preparing micro-particles in accordance with the present invention.

Before the present compounds, compositions, formulations, devices, methods, or uses are disclosed and described, it is to be understood that the aspects described below are not limited to specific compounds, compositions, formulations, devices, methods, or uses as such may, of course, vary. It is also to be understood that the terminology used herein is for the purpose of describing particular aspects only and is not intended to be limiting.

It must be noted that, as used in the specification and the appended claims, the singular forms "a," "an" and "the" include plural referents unless the context clearly dictates otherwise. Thus, for example, reference to "an active agent" includes mixtures of two or more such agents, and the like.

The present invention relates to a method for preparing micro-particles having a uniform size and narrow size distributions. The present invention further relates to a method for preparing micro-particles using a double emulsion technique combining a membrane and a micro-sieve.

In an embodiment, the present invention relates to a method for preparing micro-particles comprising: (a) preparing a first phase comprising an active agent; (b) preparing a second phase comprising a carrier and a solvent; (c) passing the first phase and the second phase through a membrane to form a primary emulsion; (d) passing the primary emulsion through a micro-sieve in a continuous phase to form a secondary emulsion; and (e) removing the solvent to form the micro-particles.

The term "micro-particles" as used herein is interchangeable with "particles," "micro-spheres" or "micro-spherical particles" and refers to particles that comprise a carrier that serves as a matrix or binder of the particle. The micro-particles may contain an active agent or other substance dispersed or dissolved within the carrier matrix. The micro-particles are usually made up of particles of a spherical shape, although sometimes the micro-particles may be irregularly shaped. The uniform micro-particles can be in the size range (diameter) from submicron to millimeter. In some embodiment, the uniform micro-particles having a mean diameter of about 0.1 µm to about 300 µm, preferably about 1 µm to about 200 µm, more preferably about 2 µm to about 150 µm, and even more preferably about 5 µm to about 100 µm are prepared, whereby administration of the micro-particles to a patient can be carried out with a standard gauge needle.

The term "narrow size distribution" as used herein refers to micro-particles having a size distribution which is substantially monodisperse. The coefficient of variation (% CV) of the micro-particles that may be obtained by a method of the instant invention is about <30%, preferably about <20%, and more preferably about <10%.

The term "active agent" as used herein is interchangeable with "bioactive agent," "pharmaceutically active agent," or "drug" and refers to an agent which has biological activity and used to treat, diagnose, cure, mitigate, prevent (i.e., prophylactically), ameliorate, modulate, or have an otherwise favorable effect on a disease, disorder, infection, and the like. Active agents also include a pro-drug which becomes bioactive or more bioactive after it has been placed in a predetermined physiological environment.

Various forms of the active agent can be used, which are capable of being released from the micro-particle into adjacent tissues or fluids. To that end, a liquid or solid active agent can be incorporated into the micro-particles described herein. As such, the active agents can be acidic, basic, or amphoteric salts. In some embodiment, the active agents can be nonionic molecules, polar molecules, or molecular complexes capable of hydrogen bonding. The active agent can be included in the micro-particles in the form of, for example, an uncharged molecule, a molecular complex, a salt, an ether, an ester, an amide, polymer drug conjugate, or other form to provide the effective biological or physiological activity.

Examples of a salt include, in the case that the active agent has a basic group such as an amino group, a salt with an inorganic acid (referred to also as an inorganic free acid) (e.g., carbonic acid, bicarbonic acid, hydrochloric acid, sulfuric acid, nitric acid, boric acid, etc.), an organic acid (referred to also as an organic free acid) (e.g., succinic acid, acetic acid, propionic acid, trifluoroacetic acid, etc.) or the like.

Examples of the salt include, in the case that the active agent has an acidic group such as a carboxyl group, a salt with an inorganic base (referred to also as an inorganic free base) (e.g., alkaline metal such as sodium and potassium, alkaline earth metal such as calcium and magnesium, etc.), an organic base (referred to also as an organic free base) (e.g., organic amines such as triethylamine, basic amino acids such as arginine, etc.) or the like. Moreover, the physiologically active peptides may form a metal complex compound (e.g., a copper complex, a zinc complex, etc.).

Examples of active agents that can be incorporated into micro-particles herein include, but are not limited to, amino acids, peptides including proteins, hormones, enzymes, antibodies, antibody fragments and the like, cytokines, vaccines, porphyrins, polysaccharides, nucleic acids such as aptamers, iRNA, DNA, RNA, siRNA, RNAi, aptamers, antisense nucleic acid or the like, antisense nucleic acid analogs or the like, dyes, lipids, cells, viruses, chemotherapeutic agent, antibiotics, antipyretic agents, analgesics, anti-inflammatory agents, antitussive expectorants, sedatives, hypnotics, neuroleptics muscle relaxants, antiepileptics, antiulcer agents, antidepressants, anti-allergic agents, cardiotonics, antiarrhythmic agents, vasodilators, hypotensive diuretics, antidiabetics, antihyperlipidemic agents, anticoagulants, hemolytics, antituberculosis agents, narcotic antagonists, bone resorption suppressors, osteogenesis promoters and angiogenesis inhibitors.

Examples of peptides include one consisting of 2 or more amino acids, preferably one consisting of 2 to 60 amino acids and having a molecular weight of about 200 to about 80,000. The peptide is preferably LH-RH (luteinizing hormone-releasing hormone) or an analog thereof. Examples of LH-RH analogs include LH-RH agonists and LH-RH antagonists.

Examples of other peptides include insulin, somatostatin, somatostatin derivative, octreotide or its pharmaceutically acceptable salt thereof such as octreotide acetate, exenatide, growth hormones, prolactin, adrenocorticotropic hormone (ACTH), ACTH derivatives (e.g., ebiratide), melanocyte-stimulating hormone (MSH), thyrotropin-releasing hormone [TRH] and salts and derivatives thereof, thyroid-stimulating hormone (TSH), luteinizing hormone (LH), follicle-stimulating hormone (FSH), vasopressin, vasopressin derivative [desmopressin], oxytocin, calcitonin, parathyroid hormone (PTH), glucagon, gastrin, secretin, pancreozymin, cholecystokinin, angiotensin, human placental lactogen, human chorionic gonadotropin (HCG), enkephalin, enkephalin derivatives, endorphin, kyotorphin, interferons (e.g., α-, β- and γ-interferons), interleukins (e.g., 1, 2, 3, 4, 5, 6, 7, 8, 9, 10, 11 and 12), tuftsin, thymopoietin, thymosin, thymostimulin, thymic humoral factor (THF), blood thymic factor (FTS) and derivative thereof, other thymic factors, tumor necrosis factor (TNF), colony-stimulating factors (e.g., CSF, GCSF, GMCSF, MCSF), motilin, dynorphin, bombesin, neurotensin, caerulein, bradykinin, urokinase, asparaginase, kallikrein, substance P, insulin-like growth factors (IGF-I, IGF-II), nerve growth factor (NGF), cell growth factors (e.g., EGF, TGF-α, TGF-β, PDGF, acidic FGF, basic FGF), bone morphogenic factor (BMP), nerve nutrition factors (e.g., NT-3, NT-4, CNTF, GDNF, BDNF), blood coagulation factors VIII and IX, lysozyme chloride, polymixin B, colistin, gramicidin, bacitracin, erythropoietin (EPO), thrombopoietin (TPO), and endothelin-antagonistic peptides.

Examples of the chemotherapeutic agents include alkylating agents (for example, cyclophosphamide, ifosfamide, nimustine, ranimustine, carboquone), antimetabolites (for example, methotrexate, 5-fluorouracil, tegafur, carmofur, UFT, doxifluridine, cytarabine, enocitabine, mercaptopurine, mercaptopurine riboside, thioguanine), anticancer antibiotic substances (for example, mitomycin, adriamycin, daunorubicin, epirubicin, pirarubicin, idarubicin, bleomycin, peplomycin, actinomycin) and plant-derived anticancer agents (for example, vincristine, vinblastine, vindesine, etoposide, camptothecine, irinotecan), cisplatin, carboplatin, nedaplatin, paclitaxel, docetaxel and estramustine.

Examples of the antibiotics include gentamicin, dibekacin, kanendomycin, lividomycin, tobramycin, amikacin, fradiomycin, sisomycin, tetracycline hydrochloride, oxytetracycline hydrochloride, rolitetracycline, doxycycline hydrochloride, ampicillin, piperacillin, ticarcillin, cefalothin, cefaloridine, cefotiam, cefsulodin, cefmenoxime, cefmetazole, cefazolin, cefotaxime, cefoperazon, ceftizoxime, mochisalactam, thienamycin, sulfazecin and aztreonam.

Examples of the antipyretic agents, analgesics and anti-inflammatory agents include salicylic acid, sulpyrine, flufenamic acid, diclofenac, indomethacin, morphine, pethidine hydrochloride, levorphanol tartrate and oxymorphone.

Examples of the antitussive expectorants include ephedrine hydrochloride, methylephedrine hydrochloride, noscapine hydrochloride, codeine phosphate, dihydrocodeine phosphate, allocramide hydrochloride, clofedanol hydrochloride, picoperidamine hydrochloride, chloperastine, protokylol hydrochloride, isoproterenol hydrochloride, sulbutamol sulfate and terbutaline sulfate.

Examples of the sedatives, hypnotics and neuroleptics include alprazolam, amylobarbitone, barbitone, bentazepam, bromazepam, bromperidol, brotizolam, butobarbitone, carbromal, chlordiazepoxide, chlormethiazole, chlorpromazine, clobazam, clotiazepam, clozapine, diazepam, droperidol, ethinamate, flunanisone, flunitrazepam, fluopromazine, flupenthixol decanoate, fluphenazine decanoate, flurazepam, baloperidol, lorazepam, lormetazepam, medazepam, meprobamate, methaqualone, midazolam, nitrazepam, oxazepam, pentobarbitone, perphenazine pimozide, prochlorperazine, sulpiride, temazepam, thioridazine, triazolam, zopiclone.

Examples of the muscle relaxants include pridinol methanesulfonate, tubocurarine chloride and pancuronium bromide.

Examples of the antiepileptics include beclamide, carbamazepine, clonazepam, ethotoin, methoin, methsuximide, methylphenobarbitone, oxcarbazepine, paramethadione, phenacemide, phenobarbitone, phenyloin, phensuximide, primidone, sulthiame, valproic acid. Examples of the antiulcer agents include metoclopramide and histidine hydrochloride.

Examples of the antidepressants include imipramine, clomipramine, trimipramine maleate, noxiptiline, phenerdine sulfate, amoxapine, maprotiline, mianserin, nortriptyline and trazodone.

Examples of the anti-allergic agents include diphenhydramine hydrochloride, chlorpheniramine maleate, tripelenamine hydrochloride, methdilazine hydrochloride, clemizole hydrochloride, diphenylpyraline hydrochloride and methoxyphenamine hydrochloride.

Examples of the cardiotonics include trans-paioxocamphor, theophyllol, aminophylline and etilefrine hydrochloride.

Examples of the antiarrhythmic agents include propranol, alprenolol, bufetolol and oxprenolol.

Examples of the vasodilators include oxyfedrine hydrochloride, diltiazem, tolazoline hydrochloride, hexobendine and bamethan sulfate.

Examples of the hypotensive diuretics include hexamethonium bromide, pentolinium, mecamylamine hydrochloride, ecarazine hydrochloride and clonidine.

Examples of the antidiabetics include glymidine sodium, glibenclamide, gliclazide, glipizide, fenformin hydrochloride, buformin hydrochloride and metformin.

Examples of the antihyperlipidemic agents include pravastatin sodium, simvastatin, clinofibrate, clofibrate, simfibrate and bezafibrate.

Examples of the anticoagulants include heparin sodium, dicoumarol, dipyridamole, nicoumalone and phenindione.

Examples of the hemolytics include thromboplastin, thrombin, menadione sodium hydrogen sulfite, acetomenaphthone, ε-aminocaproic acid, tranexamic acid, carbazochrome sodium sulfonate and adrenochrome monoaminoguanidine methanesulfonate.

Examples of the antituberculosis agents include isoniazid, ethambutol and p-aminosalicylic acid.

Examples of the narcotic antagonists include levallorphan tartrate, nalorphine hydrochloride and naloxone hydrochloride.

Examples of the osteogenesis promoters include polypeptides such as BMP, PTH, TGF-β and IGF-1, and (2R,4S)-(−)-N-[4-(diethoxyphosphorylmethyl)phenyl]-1,2,4,5-tetrahydro-4-methyl-7,8-methylenedioxy-5-oxo-3-benzothiepine-2-carboxamide and 2-(3-pyridyl)-ethane-1,1-diphosphonic acid, Examples of the angiogenesis suppressors include angiogenesis-suppressing steroid, fumagillin and fumagillol.

In some embodiment, the active agent may be water-soluble or water-dispersible. In some embodiment, the active agent may be soluble or dispersible in a solvent such as organic solvent or inorganic solvent.

The water-soluble active agent in the practice of this invention is a drug which is hydrophilic and has a solubility in water at room temperature (i.e., about 25° C.) of more than 200 micrograms per ml.

The water-dispersible active agent in the practice of this invention is a drug which is hydrophobic and has a solubility in water at room temperature (i.e., about 25° C.) of no more than (i.e., less than or equal to) 200 micrograms per ml.

In some embodiment, the active agent is preferably a peptide, more preferably LH-RH or an analog thereof, still more preferably leuprolide or its pharmaceutically acceptable salt thereof, such as leuprolide acetate.

In some embodiment, the first phase is an aqueous phase comprising an aqueous solvent. The active agent may be dissolved or dispersed in the aqueous solvent. One non-limiting example of the aqueous solvent is water. In some embodiment, water can be mixed with another miscible solvent, for example, ethanol, methanol, DMSO, DMF, isopropyl alcohol, among many other water-miscible polar solvents. In some embodiment, the first phase may further comprise other excipients, such as buffers, salts, sugars, surfactants, emulsifiers and/or viscosity-modifying agents, or combinations thereof.

The active agent may be present in the first phase in any desired % w/w. For example, the active agent may be present in the first phase in about 1% to about 90% w/w, including without limitation, about 5%, 10%, 15%, 20%, 25%, 30%, 35%, 40%, 50%, 60%, 70%, or 80% % w/w.

The term "carrier" as used herein refers to a biodegradable and biocompatible polymer or a lipid that captures, encapsulates, binds or otherwise contains the active agent that is to be released onsite.

The suitable biodegradable polymers include, but are not limited to, poly(glycolic acid), poly(d,l-lactic acid), poly(l-lactic acid), copolymers of the foregoing including poly(d,l-lactide-co-glycolide) (PLGA), poly(aliphatic carboxylic acids), copolyoxalates, poly(caprolactone), poly(dioxanone), poly(ortho carbonates), poly(acetals), poly(lactic acid-caprolactone), polyorthoesters, poly(glycolic acid-caprolactone), polyanhydrides and polyphosphazines, or derivatives thereof, or combinations thereof.

In some embodiment, the biodegradable polymer comprises block copolymers of hydrophilic and hydrophobic polymers.

In some embodiment, the inherent viscosity of the biodegradable polymer may be in the range from about 0.1 to about 2.0 dL/g. In some embodiment, the range may be from about 0.1 to about 1.0 dL/g.

In some embodiment, the molecular weight of the biodegradable polymer is in the range of about 1,000 to about 500,000 daltons, preferably about 5,000 to about 100,000 daltons, more preferably about 10,000 to about 50,000 daltons.

In some embodiment, the biodegradable polymer may be poly(d,l-lactic acid) with inherent viscosity of about 0.2 dL/g and molecular weight of about 17,000 daltons. The suitable product commercially available is Purasorb® PDL 02A.

In some embodiment, the biodegradable polymer may be poly(d,l-lactide-co-glycolide) or PLGA. The molar ratio of lactide to glycolide may be in the range of about (45-95): (5-55). In another embodiment, the molar ratio of lactide to glycolide may be 50:50, 65:35, 75:25 and 85:15.

The suitable lipids include, but are not limited to, phospholipids, diglycerides, glycolipids, single lipids such as sphingomyelin and glycosphingolipid, and cholesterol, or derivatives thereof, or combinations thereof.

In some embodiment, the second phase is an oil phase comprising an organic solvent. The carrier may be dissolved or dispersed in the solvent. Generally, the organic solvent can be selected based on the carrier solubility or polymer dispersability in that solvent. Suitable solvents include, but are not limited to, dichloromethane, chloroform, cyclohexane, 1,2-dichloroethane, benzene, butyl acetate, carbon tetrachloride, di-ethyl ether, heptane, hexane, methyl-t-butyl ether, methyl ethyl ketone, pentane, toluene, xylene, trichlorethylene, ethyl acetate, benzyl alcohol, isopropyl acetate, acetonitrile, tetrahydrofuran, isopropanol, methanol, acetone, toluene, pentyl acetate, hexyl acetate, propyl formate, isopropyl formate, methyl propionate, propyl acetate and ethanol, or combinations thereof. In some embodiment, the second phase may further comprise additives such as co-solvents, surfactants, emulsifiers, or combinations thereof, among other additives.

The carrier may be present in the second phase in any desired % w/w. For example, the carrier may be present in the second phase in about 1% to about 90% w/w, including without limitation, about 5%, 10%, 15%, 20%, 25%, 30%, 35%, 40%, 50%, 60%, 70%, or 80% % w/w.

The first phase and the second phase are combined to form the w/o emulsion (i.e., the primary emulsion). The w/o emulsion comprises the first phase comprising the active agent as the internal phase, which is substantially surrounded by the oil phase comprising the carrier. In some embodiment, the w/o emulsion may be prepared by passing and recirculating the first phase and the second phase through the membrane.

The term "membrane" as used herein refers to a multi-dimensional structure with defined pore size and made of a material selected from the group consisting of ceramics, metals, porous glass and polymers of high molecular weight. In some embodiment, the metals include, but are not limited to, stainless steel, monel, inconel, aluminum, titanium, nickel, platinum, palladium, rhodium, copper, chromium, brass and alloys of the foregoing. In some embodiment, the polymers include, but are not limited to, thermoset resins, polytetrafluoroethylene (PTFE), polyether ether ketone (PEEK), poly(carbonate), poly(propylene) and perfluoroelastomer. The nature of the membrane for use in accordance with the invention can be varied depending on the nature of the micro-particles.

In some embodiment, the membrane having diameter of about 40 mm to about 60 mm and thickness of about 0.01 to about 1 mm. The dimensions of the membrane for use in accordance with the invention can be adjusted based on the production scale of micro-particles.

In some embodiment, the membrane having a mean pore size from about 0.01 µm to about 200 µm. In some embodiment, the membrane having a mean pore size from about 0.1 µm to about 80 µm, preferably between about 1 µm to about 50 µm, more preferably about 8 µm to about 21 µm. In some embodiment, the membrane having a mean pore size from about 21 µm to about 50 µm.

In some embodiment, the membrane may be in any form including, but not limited to, a sheet, a tube and a plate. In some embodiment, the membrane has hydrophilic or hydrophobic surface.

Figure 1B:
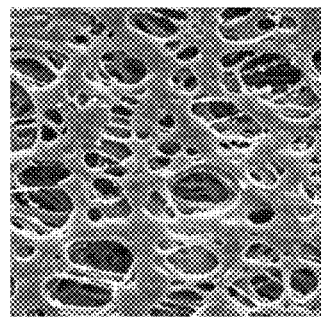
Figure 1C:
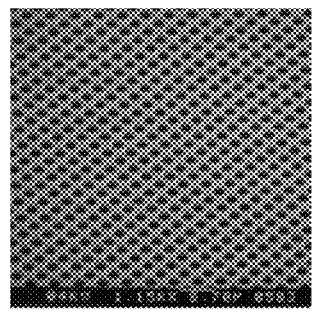

In some embodiment, the membrane may be selected from the group including, but not limited to, interwoven fiber (IWF), open cell structure (OCS), micro-sieve, perforated structure and the like. FIGS. 1A-1C show one embodiment of an interwoven fiber (IWF), an open cell structure (OCS), and a micro-sieve suitable for preparing microparticles in accordance with the present invention.

The term "Interwoven fiber" as used herein refers to plurality of interwoven threads defining a mesh screen. In some embodiment, the interwoven fiber is made of stainless steel and having diameter of about 47 mm and thickness of about 0.1 mm.

The term "Open cell structure" as used herein refers to a plain porous screen filter. In some embodiment, the open cell structure is made of polytetrafluoroethylene (PTFE) and having diameter of about 47 mm and thickness of about 0.1 mm.

The term "micro-sieve" as used herein refers to a microchannel device having strictly defined pores or slits manufactured by photolithography or similar techniques as applied in e.g. semiconductor technology. In some embodiment, the micro-sieve is made of silicone and having diameter about of about 47 mm and thickness of about 0.5 mm. Specific embodiments of micro-sieve that can be employed are described in European Patent No. 1 755 773 by applicant that is incorporated herein by reference.

In some embodiment, the first phase and the second phase are passed through the membrane at a flow rate from about 0.01 ml/min/cm$^2$ to about 100 ml/min/cm$^2$. In some embodiment, the flow rate is from about 0.05 ml/min/cm$^2$ to about 50 ml/min/cm$^2$. In some embodiment, the flow rate is from about 5 ml/min/cm$^2$ to about 40 ml/min/cm$^2$, preferably about 10 ml/min/cm$^2$ to about 30 ml/min/cm$^2$, and more preferably about 12.5 ml/min/cm$^2$ to about 17.5 ml/min/cm$^2$.

In some embodiment, the first phase and the second phase are passed by means of pump in an aseptic closed circulation to form primary emulsion. The pumps, include, but are not limited to, peristaltic pump, centrifugal pump, gear pump and piston pump.

In some embodiment, the primary emulsion containing micro-droplets having a mean diameter of about <100 µm, preferably mean diameter of about <40 µm and more preferably mean diameter of about <20 µm.

In some embodiment, the active agent is present in the primary emulsion from about 0.1% w/w to about 25% w/w of the primary emulsion. In some embodiment, the active agent is present in the primary emulsion from about 0.5% w/w to about 10% w/w of the primary emulsion. In some embodiment, the active agent is present in the primary emulsion from about 1% w/w to about 5% w/w of the primary emulsion.

In some embodiment, the carrier is present in the primary emulsion from about 1% w/w to about 50% w/w of the primary emulsion.

In some embodiment, other methods may be selected to form the primary emulsion including, but not limited to, static mixer, homogenizer, propeller, impeller, stirrer and the like.

In some embodiment, the continuous phase is an aqueous phase comprising an aqueous solvent. The aqueous phase may comprise any suitable aqueous solvent. One non-limiting example of an aqueous solvent is water. In some embodiment, water can be mixed with another miscible solvent, for example, ethanol, methanol, DMSO, DMF, isopropyl alcohol, among many other water-miscible polar solvents. In some embodiment, the continuous phase may further comprise other excipients, such as buffers, salts, sugars, surfactants and/or viscosity-modifying agents, or combinations thereof.

Once the micro-droplets are formed in the continuous phase, it is important to prevent them from aggregating. To that end, the continuous phase comprises a stabilizer for substantially preventing the micro-droplets from aggregating. As a result, the mono disperse nature of the droplets are maintained in the continuous phase. In some embodiment, the stabilizers may be surfactants or hydrophilic colloids include, but are not limited to, polyvinyl alcohol, gelatin, polyvinyl pyrrolidone, sorbitan esters and their ethoxylates such as span and tween, celluloses and their derivatives such as carboxymethyl cellulose, and polyethylene glycols, or combinations thereof. The concentration of stabilizer in the continuous phase may be from about 0.1% to about 10% w/w of the continuous phase, depending upon the stabilizer, the primary emulsion, and the continuous phase used. In some embodiment, the continuous phase may be about 0.1 to about 10 w/w, more preferably about 0.5% w/w to about 5% w/w solution of polyvinyl alcohol in water.

The primary emulsion and the continuous phase are combined to form a w/o/w double emulsion (i.e., the secondary emulsion). The w/o/w emulsion comprises the first phase comprising the active agent as the internal phase, which is substantially surrounded by the second phase comprising the carrier, the second phase being substantially surrounded by the continuous phase. In some embodiment, the w/o/w emulsion can be prepared by passing the primary emulsion through the micro-sieve in the continuous phase.

In some embodiment, other methods may be selected to form the secondary emulsion including, but not limited to, static mixer, homogenizer, propeller, impeller, stirrer and the like.

In some embodiment, the primary emulsion and the continuous phase are passed by means of pump in an aseptic closed circulation to form secondary emulsion. The pumps include, but are not limited to, peristaltic pump, centrifugal pump, gear pump and piston pump.

Once the secondary emulsion is formed, micro-particles can be typically formed from the secondary emulsion by removing the organic solvent. The organic solvent can be removed by any suitable methods. In some embodiment, the organic solvent may be removed by extracting the organic solvent with an extraction liquid, such as water. In some embodiment, the organic solvent can be removed by drying, such as by spray drying, drying under reduced pressure, solvent evaporation, freeze-drying or combinations thereof. The solvent removal may also be performed using a continuous process such as a continuous liquid extraction process.

In some embodiment, the organic solvent is evaporated to harden the micro-particles. The solvent removal by evaporation can be controlled by temperature, time and pressure. In some embodiment, the temperature may be about 4° C. to about 100° C. and the time may be about 1 hour to about 24 hours.

In some embodiment, the secondary emulsion may be an o/w/o emulsion. For example, an active agent can be dissolved or dispersed in an oil phase, and a carrier can be dissolved or dispersed in an aqueous phase. Next, an oil phase can be added to form a double emulsion. Any of the process steps described above can be used for preparing o/w/o double emulsion.

In some embodiment, the primary emulsion may be a w/o emulsion, an o/w emulsion, or any suitable emulsion. In some embodiment, the secondary emulsion may be a w/o/w emulsion, an o/w/o emulsion, or any suitable emulsion.

The amount of active agent incorporated in the micro-particles ranges from about 1% w/w to about 50% w/w, preferably about 5% w/w to about 25% w/w, more preferably about 8% w/w to about 15 w/w of the micro-particles.

EXAMPLES

The following examples are included to demonstrate particular embodiments of the invention. It should be appreciated by those of skill in the art that the techniques disclosed in the examples which follow represent techniques discovered by the inventors to function well in the practice of the invention, and thus can be considered to constitute preferred modes for its practice. However, those of skill in the art should, in light of the present disclosure, appreciate that many changes can be made in the specific embodiments which are disclosed and still obtain a like or similar result without departing from the spirit and scope of the invention.

Example 1

A first phase is prepared by dissolving an active agent in an aqueous solvent. Alternatively, first phase may be prepared by dispersing an active agent in an aqueous solvent. In such a dispersion, the active agent is only slightly soluble in the aqueous solvent. The second phase is prepared by dissolving a carrier in an organic solvent. The First phase and the second phase are passed and recirculated through a membrane to form a primary emulsion. The primary emulsion is then passed through a micro-sieve in a continuous phase to form a secondary emulsion. The organic solvent is removed from the secondary emulsion resulting in the formation of hardened micro-particles. The micro-particles are then isolated from the aqueous solution by any convenient means of separation; the fluid can be decanted from the micro-particles or the micro-particle suspension can be filtered or a sieve column can be used. Various other combinations of separation techniques can be used, if desired. The micro-particles are then dried using conventional drying techniques, and further size isolation may be carried out.

Example 2

Figure 4:
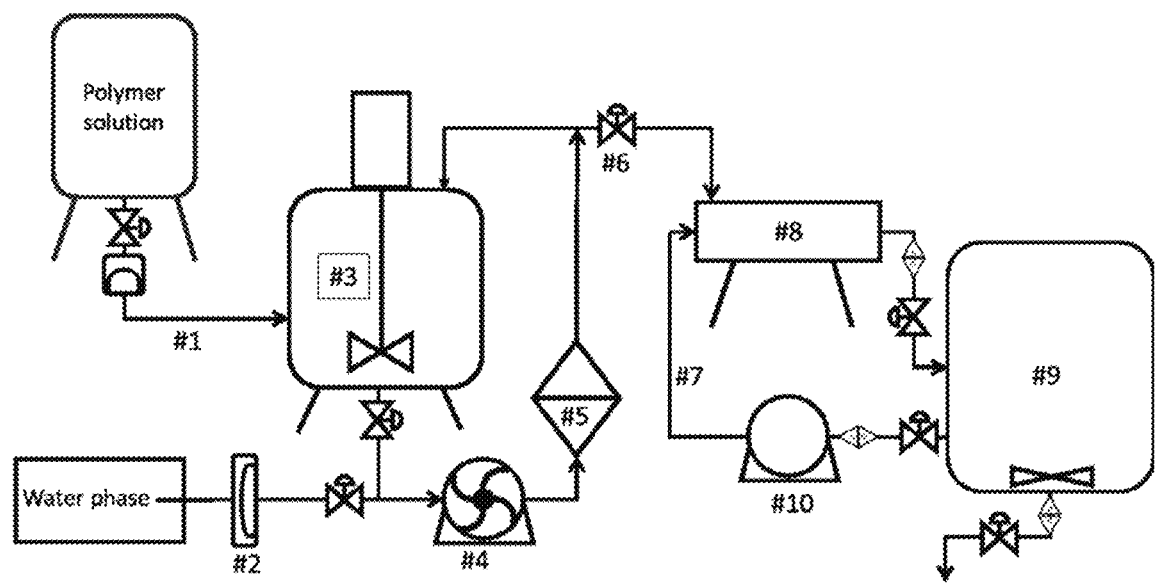
FIG. 4 shows a set up for carrying out a method for preparing micro-particles of the present invention.

A set up for carrying out method for preparing micro-particles is illustrated in FIG. 4. A first phase (Aqueous phase) containing 34% w/w leuprolide acetate is prepared by dissolving the leuprolide acetate in water. A second phase (Polymer solution) containing 25% w/w of poly(d,l-lactic acid) (Purasorb® PDL 02A) is prepared by dissolving the poly(d,l-lactic acid) in dichloromethane (DCM). A continuous phase containing 4% w/w of polyvinyl alcohol is prepared by dissolving the polyvinyl alcohol in water.

The second phase is pumped through the inlet line (1) to a closed vessel (3). The first phase is pumped through the inlet line (2). The first phase and the second phase are passed and recirculated by the pump (4) through an interwoven fiber (5) having mean pore size of 10 μm to 12 μm at a flow rate of 15 ml/min/cm² to form primary emulsion. Valve (6) is opened and the primary emulsion is passed at a flow rate of 0.67 ml/min/cm² through a 40 μm micro-sieve (8) in the continuous phase circulated under the micro-sieve to produce the secondary emulsion and then transferred in a vessel (9). The continuous phase from the reservoir (9) is circulated by the pump (10) through the inlet line (7) under the micro-sieve at a flow rate of 17 L/hour. After production of the secondary emulsion the DCM is removed and the hardened micro-particles are separated. The micro-particles are analyzed for particle size using Coulter Counter Multi-sizer®.

Example 3

Figure 2:
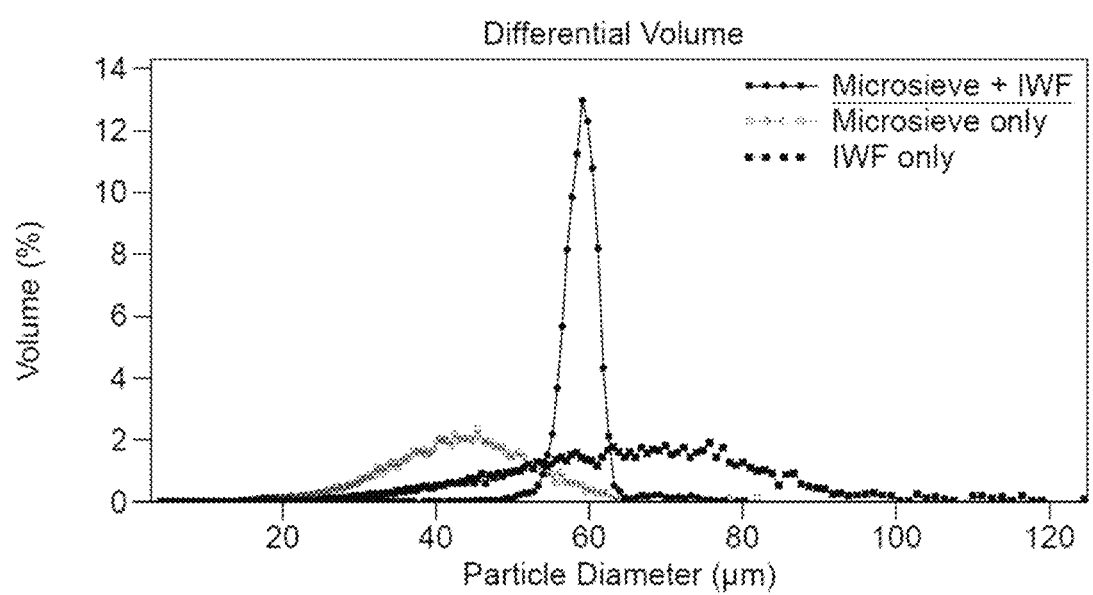
FIG. 2 depicts a graph of size distributions of micro-particles prepared using micro-sieve only, using IWF only and using both IWF and micro-sieve.

The procedure of example 2 is repeated using micro-sieve only, using IWF only and using both IWF and micro-sieve. Table 1 and FIG. 2 demonstrate that substantially monodisperse micro-particles are obtained by using both IWF and micro-sieve.

TABLE 1

| Sr. No. | Test | Mean micro-particle diameter (μm) | Coefficient of variation (% CV) |
|---|---|---|---|
| 1. | IWF only | 65 | 54.1 |
| 2. | Micro-sieve only | 41 | 24.3 |
| 3. | IWF and micro-sieve | 61 | 8.5 |

Example 4

Figure 3:
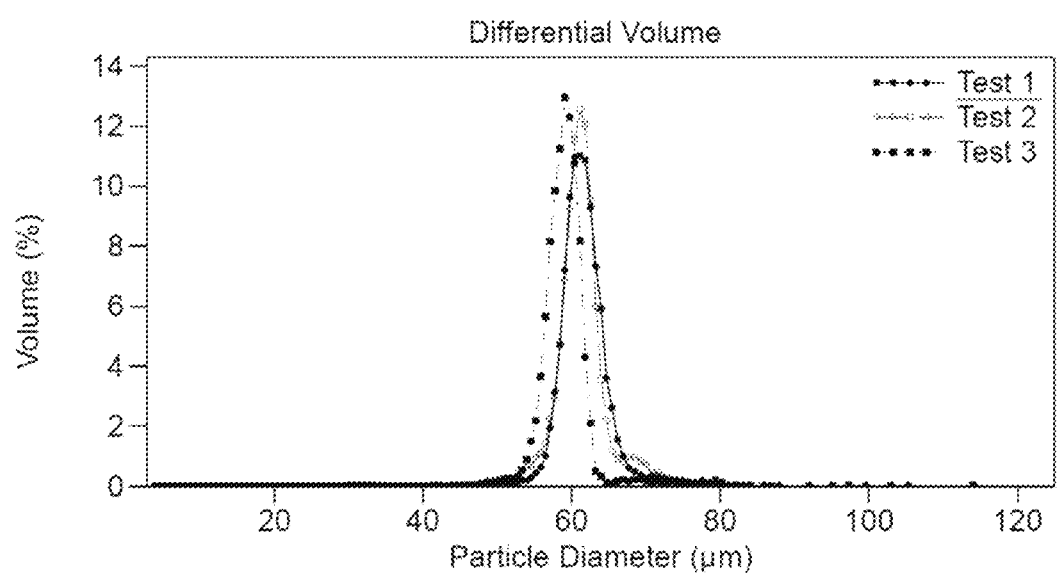
FIG. 3 depicts a graph of size distributions of three reproducible batches of micro-particles.

The procedure of example 2 is repeated in triplicate. Table 2 and FIG. 3 demonstrate reproducibility of substantially monodisperse micro-particles.

TABLE 2

| Sr. No. | Test | Mean micro-particle diameter (μm) | Coefficient of variation (% CV) |
|---|---|---|---|
| 1. | Test 1 | 61 | 8.5 |
| 2. | Test 2 | 60 | 9.2 |
| 3. | Test 3 | 59 | 7 |

Example 5

A first phase (Aqueous phase) containing 25% w/w leuprolide acetate is prepared by dissolving the leuprolide acetate in water. The second phase (Polymer solution) containing 20% w/w of poly(d,l-lactide-co-glycolide) polymer (monomer ratio: 75/25, average mol. wt.: 17000, viscosity: 0.2 dL/g) is prepared by dissolving the polymer in dichloromethane (DCM). The continuous phase containing 0.5% w/w of polyvinyl alcohol is prepared by dissolving the polyvinyl alcohol in water.

The second phase is pumped through the inlet line (1) to a closed vessel (3). The first phase is pumped through the inlet line (2). The first phase and second phase are passed and recirculated by the pump (4) through the interwoven fiber (5) having mean pore size of 19 μm to 21 μm at a flow rate of 17 ml/min/cm² to form primary emulsion. Valve (6) is opened and the primary emulsion is passed at a flow rate of 0.55 ml/min/cm² (7) through a 30 μm micro-sieve (8) in the continuous phase (7) circulated under the micro-sieve to produce the secondary emulsion that is transferred in a vessel (9). The continuous phase from the reservoir (9) is circulated by the pump (10) through the inlet line (7) under the micro-sieve at a flow rate of 15 L/hour. After production of the secondary emulsion the DCM is removed and the hardened micro-particles are separated.

The invention claimed is:

1. A method for preparing micro-particles comprising:
    (a) preparing a first phase comprising an active agent;
    (b) preparing a second phase comprising a carrier and a solvent;
    (c) passing the first phase and the second phase through a membrane to form a primary emulsion;
    (d) passing the primary emulsion through a micro-sieve in a continuous phase to form a secondary emulsion; and
    (e) removing the solvent to form the micro-particles.

2. The method according to claim 1, wherein the active agent is water-soluble or water-dispersible.

3. The method according to claim 1, wherein the active agent is a peptide or a nucleic acid.

4. The method according to claim 3, wherein the peptide is from the group consisting of leuprolide acetate, octreotide acetate and exenatide.

5. The method according to claim 1, wherein the active agent is present in the primary emulsion from about 0.1% w/w to about 25% w/w of the primary emulsion.

6. The method according to claim 1, wherein the carrier is a biodegradable: polymer or a lipid.

7. The method according to claim 6, wherein the biodegradable polymer is selected from the group consisting of poly(glycolic acid), poly(d,l-lactic acid), poly(l-lactic acid), copolymers of the foregoing, poly(aliphatic carboxylic acids), copolyoxalates, poly(caprolactone), poly(dioxanone), poly(ortho carbonates), poly(acetals), poly(lactic acid-caprolactone), polyorthoesters, poly(glycolic acid-caprolactone), polyanhydrides and polyphosphazines, or derivatives thereof, or combinations thereof.

8. The method according to claim 6, wherein the lipid is selected from the group consisting of phospholipids, diglycerides, glycolipids, sphingomyelin, glycosphingolipid and cholesterol, or derivatives thereof, or combinations thereof.

9. The method according to claim 1, wherein the solvent is selected from the group consisting of dichloromethane, chloroform, cyclohexane, 1,2-dichloroethane, benzene, butyl acetate, carbon tetrachloride, di-ethyl ether, heptane, hexane, methyl-t-butyl ether, methyl ethyl ketone, pentane, toluene, xylene, trichlorethylene, ethyl acetate, benzyl alcohol, isopropyl acetate, acetonitrile, tetrahydrofuran, isopropanol, methanol, acetone, toluene, pentyl acetate, hexyl acetate, propyl formate, isopropyl formate, methyl propionate, propyl acetate and ethanol, or combinations thereof.

10. The method according to claim 1, wherein the membrane is selected from the group consisting of an interwoven fiber, an open cell structure and a micro-sieve.

11. The method according to claim 10, wherein the membrane has a mean pore size from about 1 μm to about 50 μm.

12. The method according to claim 1, wherein the first phase and the second phase are passed through the membrane at a flow rate from about 0.05 ml/min/cm² to about 50 ml/min/cm².

13. The method according to claim 1, wherein the continuous phase is an aqueous phase comprising a stabilizer.

14. The method according to claim 13, wherein the stabilizer is selected from the group consisting of polyvinyl alcohol, gelatin, polyvinyl pyrrolidone, sorbitan esters and their ethoxylates, celluloses and their derivatives, and polyethylene glycols, or combinations thereof.

* * * * *